United States Patent
Pico

(10) Patent No.: US 9,897,522 B2
(45) Date of Patent: Feb. 20, 2018

(54) METHOD FOR DETERMINING MECHANICAL PROPERTIES OF A MATERIAL

(71) Applicant: SCHLUMBERGER TECHNOLOGY CORPORATION, Sugar Land, TX (US)

(72) Inventor: Yamid Pico, Moscow (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 28 days.

(21) Appl. No.: 15/105,960

(22) PCT Filed: Dec. 18, 2013

(86) PCT No.: PCT/RU2013/001132
§ 371 (c)(1),
(2) Date: Jun. 17, 2016

(87) PCT Pub. No.: WO2015/094007
PCT Pub. Date: Jun. 25, 2015

(65) Prior Publication Data
US 2017/0030814 A1  Feb. 2, 2017

(51) Int. Cl.
*G01H 1/00* (2006.01)
*G01N 29/04* (2006.01)
(Continued)

(52) U.S. Cl.
CPC .............. *G01N 3/405* (2013.01); *G01H 1/00* (2013.01); *G01N 3/40* (2013.01); *G01N 3/42* (2013.01);
(Continued)

(58) Field of Classification Search
CPC ........ G01H 1/00; G01N 29/045; G01N 29/11; G01N 3/42; G01N 3/40; G01N 3/405;
(Continued)

(56) References Cited

U.S. PATENT DOCUMENTS 2,582,314 A    1/1952  Doll
2,712,627 A    7/1955  Doll
(Continued)

FOREIGN PATENT DOCUMENTS

DE    4306243 A1    9/1993
JP    02264843 A    10/1990
(Continued)

OTHER PUBLICATIONS

Franco, J.L. Arroyo et al, "Sonic Investigations in and Around the Borehole", Oilfield Review, (Spring 2006), 20 pp.
(Continued)

*Primary Examiner* — J M Saint Surin

(57) ABSTRACT

A tool having at least one vibration sensor and at least one standoff is disposed in a contact with a material and the at least one standoff of the tool is pushed into the material. Vibration is excited by the at least one vibration source and at least one coupling frequency of the tool is measured by the at least one vibration sensor. Based on the determined coupling frequency determining a contact stiffness of the at least one standoff and the mechanical properties of the material are determined taking into account mechanical properties of the at least one standoff.

6 Claims, 3 Drawing Sheets

(51) Int. Cl.
*G01N 29/11* (2006.01)
*G01N 3/40* (2006.01)
*G01N 3/42* (2006.01)

(52) U.S. Cl.
CPC ........... *G01N 29/045* (2013.01); *G01N 29/11* (2013.01); *G01N 2203/0005* (2013.01); *G01N 2291/02827* (2013.01); *G01N 2291/101* (2013.01)

(58) Field of Classification Search
CPC . G01N 2291/02827; G01N 2203/0005; G01N 2291/101
USPC .......................................................... 73/573
See application file for complete search history.

(56) References Cited

U.S. PATENT DOCUMENTS

| | | | | |
|---|---|---|---|---|
| 7,066,282 | B2* | 6/2006 | Chen | G01V 3/24 166/250.11 |
| 2005/0257611 | A1* | 11/2005 | Fogal | E21B 49/10 73/152.22 |
| 2006/0106541 | A1* | 5/2006 | Hassan | G01V 1/48 702/6 |
| 2013/0124176 | A1* | 5/2013 | Fox | G06F 17/00 703/7 |
| 2014/0152659 | A1* | 6/2014 | Davidson | G06T 17/05 345/420 |

FOREIGN PATENT DOCUMENTS

| | | |
|---|---|---|
| JP | 2004361251 A | 12/2004 |
| RU | 2108561 C1 | 4/1998 |
| SU | 1597687 A1 | 10/1990 |

OTHER PUBLICATIONS

Haldorsen, Jakob B.U. et al, "Borehole Acoustic Waves", Oilfield Review, (Spring 2006), 10 pp.

Brie, Alain et al., "New Directions in Sonic Logging", Oilfield Review, (Spring 1998), 16 pp.

* cited by examiner a)					b)

METHOD FOR DETERMINING MECHANICAL PROPERTIES OF A MATERIAL

FIELD OF THE INVENTION

This invention relates to methods for determination of mechanical properties of materials, namely Young modulus and Poisson ratio, and can be used, for example, for studying a formation surrounding a borehole, a ground floor or any surface for which material properties are to be measured.

BACKGROUND OF THE INVENTION

Many none destructive methods for determining mechanical properties of materials are known, such as wave propagation methods and micro/nano indentation methods (see, for example, General relationship between contact stiffness, contact depth, and mechanical properties for indentation in linear visco elastic solids using axisymetric indenters of arbitrary profile, Yang-Tse Chenga, Che-Min Cheng. 2005, APPLIED PHYSICS LETTERS 87, 111914, or An analysis of nanoindentation in linearly elastic solids. B. Poon a, D. Rittel b, G. Ravichandran. s.l.: International Journal of Solids and Structures 45, 2008, pp. 6018-6033). The known method provides for measuring hardness based on loading and unloading of specimens and can be accomplished only in laboratories.

The proposed method provides for easy and fast determination of mechanical properties of materials which requires only information on dynamic properties of a tool being used and can be done in situ.

SUMMARY OF THE INVENTION

The method for determining mechanical properties of a material comprises disposing a tool having at least one vibration sensor and at least one standoff in a contact with a material. Then the at least one standoff of the tool is pushed into the material and vibration is excited by at least one vibration source. At least one coupling frequency of the tool is measured by the at least one vibration sensor and a contact stiffness of the at least one standoff is determined based on the determined coupling frequency. The mechanical properties of the material are determined based on the determined contact stiffness of the at least one standoff and on dynamic properties of the at least one standoff.

The vibration source can be disposed inside or outside the tool.

The material can be a formation surrounding a borehole.

The tool can be clamped to the material.

The mechanical properties of the material and of the at least one standoff are Poisson ratio and Young modulus of the material and of the at least one standoff.

BRIEF DESCRIPTION OF THE DRAWINGS

The invention is explained by drawings where.

DETAILED DESCRIPTION OF THE PREFERRED EMBODIMENTS

Figure 1:
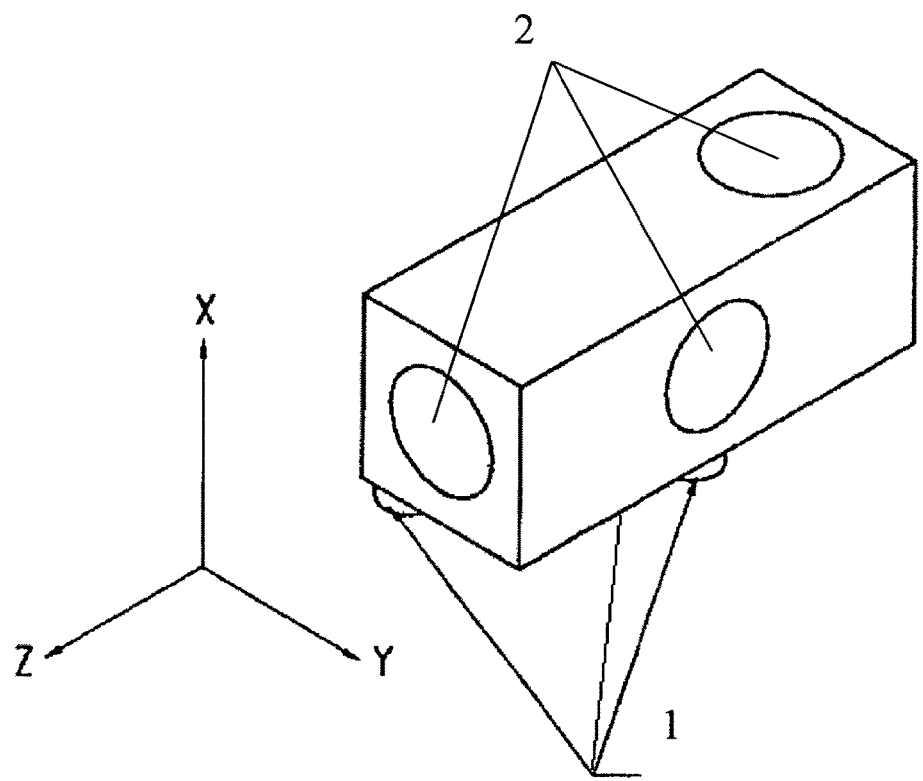
FIG. 1(a) shows an example of a tool with three standoffs.

On FIG. 1 it is shown an example of a tool according to the proposed invention. The tool has standoffs (contact points) 1 and holes 2 for vibration sensors. The vibration sensors can be geophones or accelerometers that can measure direction of vibration. At least one vibration source also can be disposed inside the tool. The vibration source can be a shaker type or any vibration device capable of generate controlled vibration in a defined wave band. All those vibration sensors and vibration sources can be located in different positions in the tool and with different orientation. This is with the purpose of having the possibility of excitation of different vibration modes. It is especially important for addressing anisotropy materials and for quality control of measurements.

Then the at least one standoff of the tool is pushed into the material and vibration is excited by the vibration source. Vibration can be excited by any external or internal vibration source. At least one coupling frequency (a frequency at which the tool starts to vibrate due to the contact (coupling)) of the tool is measured by the at least one vibration sensor disposed inside the tool. The coupling frequencies are measured by examining a spectrum of the acquired readings of the vibration sensors.

A clamping force and a mass and moment of inertia of the tool are known, a shape and mechanical properties of the standoffs are also known. A combination of dynamic equations and equations for contact can be solved to find the unknowns—Young modulus and Poisson ratio of the material where the tool is located (and if necessary clamped). For the case of an isotropy material, the configuration can be freely chosen and can be used two or more standoffs for quality control. Knowing two first coupling frequencies of a particular configuration of the tool allows to calculate the Young modulus and Poisson coefficient of the material where the tool is located. Even with only the first coupling frequency registered for any configuration, it is possible to have a good approximation of the Young modulus regarding a good initial estimation of Poisson ratio. For the case of anisotropic material the larger the number of the frequencies, the more is the number of material properties that can be determined.

Below it is described a procedure for obtaining the equations for the case of using a tool with three standoffs shown on FIG. 1.

Figure 2:
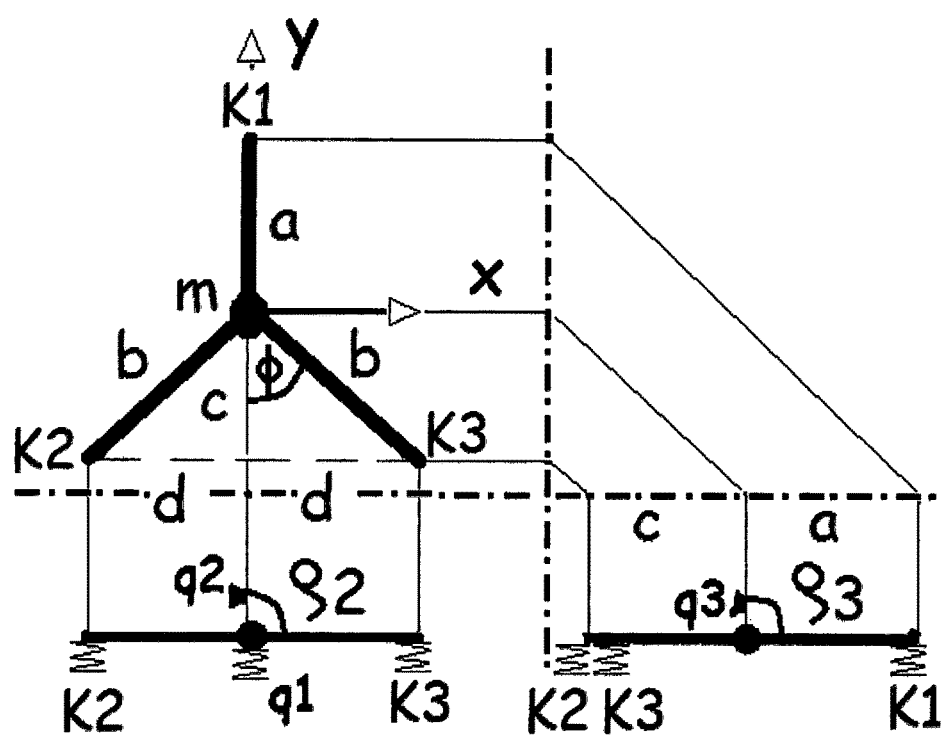
FIG. 2 shows a dynamic diagram for the tool showed in FIG. 1.

Equations of motion give the relationship to calculate coupling frequencies (Lagrange equation of the system) for the tool. We obtain:

$$\Omega_{coup1} = \sqrt{\frac{k_1 + k_2 + k_3}{m}} \quad (1)$$

$$\Omega_{coup2} = \sqrt{\frac{k_2 d^2 + k_3 d^2}{I_2}}$$

$$\Omega_{coup3} = \sqrt{\frac{k_2 c^2 + k_3 c^2 + k_1 a^2}{I_3}}$$

where $\Omega_{coup1}, \Omega_{coup2}, \Omega_{coup3}$ are the coupling frequencies of the tool, $k_1, k_2, k_3$-contact stiffness of three standoffs. Based on specific design it is possible to achieve very similar values of the contact stiffness so we can assume them equal: $k_1=k_2=k_3$. Parameters d, c and a are distances from a center of mass to the location of the standoffs (see FIG. 2); m is a mass of the tool, and $I_2, I_3$ are moments of inertia of the tool body/package respect to an axis of rotation. Making several measurements of the frequencies, a more robust value of the frequencies can be obtained.

Below, based on contact theory several relationships for the contact stiffness are derived, the main relationship is $$k = 2E_r \frac{\sqrt{A}}{\sqrt{\pi}}$$

where k is a contact stiffness and A is a projected contact area.

$E_r$ is a reduced stiffness modulus that is defined as $$\frac{1}{E_r} = \frac{(1-\upsilon)}{E} + \frac{(1-\upsilon')}{E'}$$

Here, $\upsilon$, E are Poisson ratio and Young modulus of the material to be tested respectively. $\upsilon'$, E' are Poisson ratio and Young modulus of the standoffs.

The definition of the contact area A depends on a shape of the standoff. It is calculated using Hertz contact theory.

Figure 3:
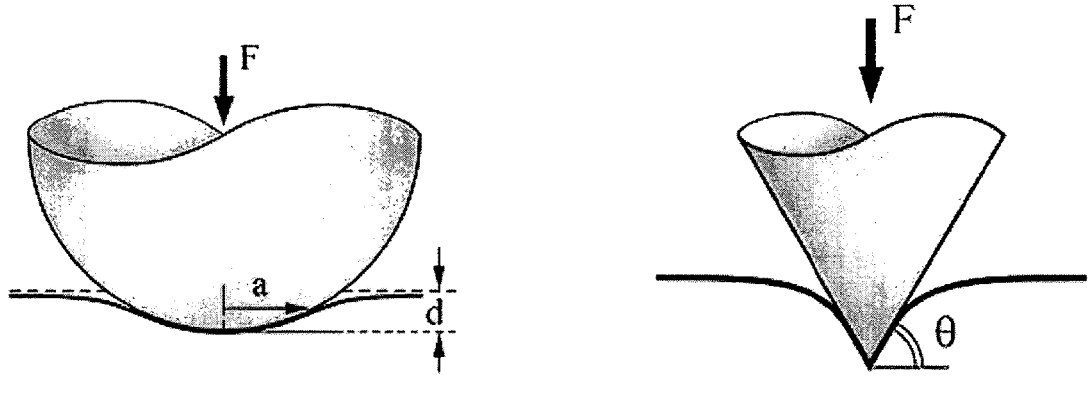
FIG. 3 shows two variants of possible shapes of the standoffs.

Bellow there are examples of calculation for two shapes of the standoffs (FIGS. 3a and 3b).

Semi Spherical Stand Off

Using Hertz contact theory, is possible to relate a clamping force of the tool to the contact area. For a shape as indicated in the FIG. 3a, an area of contact will be $$A^2 = \pi \cdot R \cdot h$$

where R is a radius of a round standoff, h is a height of penetration of the standoff into the material. A force is related to the reduced modulus and area of contact by $$F = \frac{A \cdot E_r \cdot R^{\frac{1}{2}} \cdot h^{\frac{3}{2}}}{3}$$

From this the following relationship is obtained $$\sqrt{A} = \left(\frac{3 \cdot F \cdot R}{4 \cdot E_r}\right)^{\frac{1}{6}}$$

Using this the relationship for the stiffness contact for the round standoff (with $\upsilon$, E) pushed with a force F into a sample (with $\upsilon'$, E') is obtained $$K = \frac{2 \cdot E_r}{\sqrt{\pi}} \left(\frac{3 \cdot F \cdot R}{4 \cdot E_r}\right)^{\frac{1}{6}}$$

The obtained value of the contact stiffness can be introduced in the formulas of the frequencies (1):

$$\begin{cases} \Omega_{coup_1} = \sqrt{\frac{\alpha}{m}} = \sqrt{\frac{2k_1 + 2k_2 + 2k_3}{m}} \\ \Omega_{coup_2} = \sqrt{\frac{\xi}{m \cdot r_2^2}} = \sqrt{\frac{k_2 \cdot d^2 + k_3 \cdot d^2}{m \cdot r_2^2}} \\ \Omega_{coup_3} = \sqrt{\frac{\eta}{m \cdot r_3^2}} = \sqrt{\frac{k_2 \cdot c^2 + k_3 \cdot c^2 + k_1 \cdot a^2}{m \cdot r_2^2}} \end{cases}$$

with $$K_{1,2,3} = \frac{2 \cdot E_r}{\sqrt{\pi}} \left(\frac{3 \cdot F \cdot R}{4 \cdot E_r}\right)^{\frac{1}{3}}$$

$E_r$ is found and then Young modulus and Poisson ratio of the tested material are determined.

Conical Stand Offs (Spikes)

As for the previous case Hertz contact theory is used to relate a clamping force to a contact area. For a shape as indicated in FIG. 3b, the area of contact will be $$A^2 = \frac{h^2 \cdot \tan(\frac{\pi}{2} - \Theta)^2}{\pi}$$

Where $\theta$ is an angle defining a sharpness of the standoffs, h-a depth of penetration into the material. The force is related to the reduced modulus and area of contact by $$F = \frac{A \cdot E_r}{2 \cdot \tan(\frac{\pi}{2} - \theta)}$$

From this the relationship is obtained $$\sqrt{A} = \left(\frac{F \cdot \tan(\frac{\pi}{2} - \theta)}{2 \cdot E_r}\right)^{\frac{1}{2}}$$

Using this the relationship for the stiffness contact for a conical standoff (with $\upsilon$, E) pushed with a force F into a casing (with $\upsilon'$, E') is obtained $$K = \frac{2 \cdot E_r}{\sqrt{\pi}} \left(\frac{2 \cdot F \cdot \tan(\frac{\pi}{2} - \theta)}{E_r}\right)^{\frac{1}{2}}$$

The obtained value of the contact stiffness can be introduced in the formulas of the frequencies (1):

$$\begin{cases} \Omega_{coup_1} = \sqrt{\frac{\alpha}{m}} = \sqrt{\frac{2k_1 + 2k_2 + 2k_3}{m}} \\ \Omega_{coup_2} = \sqrt{\frac{\xi}{m \cdot r_2^2}} = \sqrt{\frac{k_2 \cdot d^2 + k_3 \cdot d^2}{m \cdot r_2^2}} \\ \Omega_{coup_3} = \sqrt{\frac{\eta}{m \cdot r_3^2}} = \sqrt{\frac{k_2 \cdot c^2 + k_3 \cdot c^2 + k_1 \cdot a^2}{m \cdot r_2^2}} \end{cases}$$

with $$K_{1,2,3} = \frac{2 \cdot E_r}{\sqrt{\pi}} \left(\frac{2 \cdot F \cdot \tan(\frac{\pi}{2} - \theta)}{E_r}\right)^{\frac{1}{2}}$$

Then it is solved for $E_r$ and then Young modulus and Poisson ratio of the tested material are determined.

The described procedure is general, for any shape or mechanical design of the tool and any shape and material of the standoffs.

The invention claimed is:

1. A method for determining mechanical properties of a material comprising:
    disposing a tool having at least one vibration sensor and at least one standoff in a contact with a material,
    pushing the at least one standoff of the tool into the material,
    exciting vibration by the at least one vibration source,
    measuring at least one coupling frequency of the tool by the at least one vibration sensor,
    determining a contact stiffness of the at least one standoff based on the determined coupling frequency and determining the mechanical properties of the material based on the determined contact stiffness of the at least one standoff and on mechanical properties of the at least one standoff.

2. The method of claim 1 wherein the at least one vibration source is disposed inside the tool.

3. The method of claim 1 wherein the at least one vibration source is disposed outside the tool.

4. The method of claim 1 wherein the mechanical properties of the material and of the at least one standoff are Poisson ratio and Young modulus of the material and of the at least one standoff.

5. The method of claim 1 wherein material is a formation surrounding a borehole.

6. The method of claim 1 wherein the tool is clamped to the material.

* * * * *